(12) United States Patent
Sterry et al.

(10) Patent No.: US 8,025,149 B2
(45) Date of Patent: Sep. 27, 2011

(54) DEVICE FOR MONITORING THE REMOVAL OF ITEMS PLACED IN COMPARTMENTS OF A BLISTER PACKAGE, IN PARTICULAR TO ASSIST A PATIENT IN FOLLOWING A PRESCRIBED PROGRAMME OF MEDICATION

(75) Inventors: Graham Sterry, Bristol (GB); Catherine Gal, Verrieres-le-Buisson (FR)

(73) Assignee: Advanced Telecare Solutions Ltd., Bristol (GB)

( * ) Notice: Subject to any disclaimer, the term of this patent is extended or adjusted under 35 U.S.C. 154(b) by 0 days.

(21) Appl. No.: 13/061,362

(22) PCT Filed: Aug. 17, 2009

(86) PCT No.: PCT/GB2009/002019
§ 371 (c)(1),
(2), (4) Date: Feb. 28, 2011

(87) PCT Pub. No.: WO2010/023430
PCT Pub. Date: Mar. 4, 2010

(65) Prior Publication Data
US 2011/0155602 A1  Jun. 30, 2011

(30) Foreign Application Priority Data
Aug. 30, 2008 (GB) .................................. 0815817.2

(51) Int. Cl.
*B65D 83/04* (2006.01)
(52) U.S. Cl. ........................................ 206/534; 206/538

(58) Field of Classification Search ................. 206/528, 206/531, 532, 534, 536, 538, 533
See application file for complete search history.

(56) References Cited

U.S. PATENT DOCUMENTS

| 5,412,372 | A | 5/1995 | Parkhurst et al. | |
|---|---|---|---|---|
| 6,574,166 | B2 * | 6/2003 | Niemiec | 368/10 |
| 2002/0017996 | A1 * | 2/2002 | Niemiec | 340/573.1 |
| 2006/0144747 | A1 | 7/2006 | Le et al. | |

FOREIGN PATENT DOCUMENTS

| DE | 38 18705 A1 | 7/1989 |
|---|---|---|
| DE | 41 34237 C1 | 4/1993 |
| EP | 0 009 280 A1 | 4/1980 |

(Continued)

OTHER PUBLICATIONS

International Search Report from PCT/GB2009/002019 dated Dec. 18, 2009 (3 pages).

(Continued)

*Primary Examiner* — Jacob K Ackun
(74) *Attorney, Agent, or Firm* — Osha • Liang LLP

(57) ABSTRACT

Described within is a device for monitoring the removal of articles contained in compartments of a standard blister package, in particular to assist a patient in following a prescribed programme of drugs. The compartments are covered with a rupturable cover. The removal of a drug out of the blister package is detected by photosensitive sensors located under the compartments, one per compartment. The device includes an opaque frame support comprising cavities which accommodate said standard blister package and covers the transparent faces of each compartment, which keeps light from the photosensitive sensors. Ambient light illuminates the photosensitive sensors when the cover of a compartment is torn and a drug removed from the compartment.

17 Claims, 3 Drawing Sheets

FOREIGN PATENT DOCUMENTS

Figure 1A:
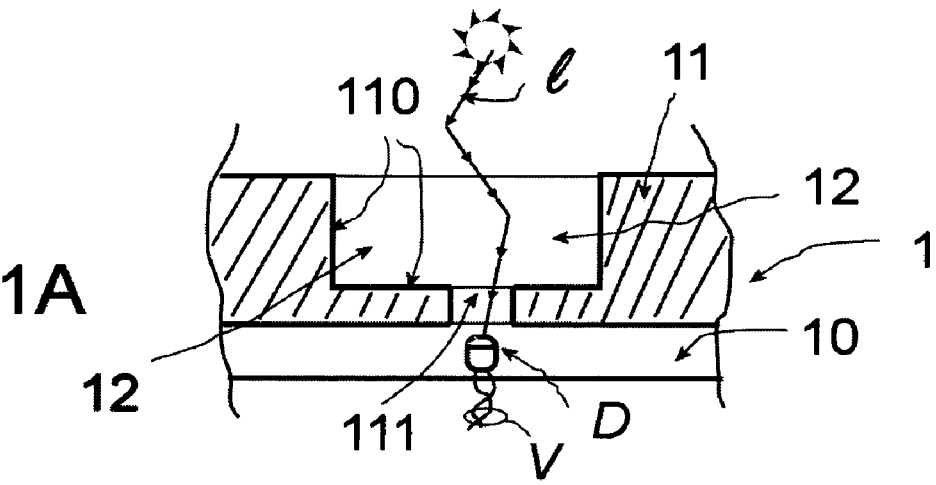

| | | |
|---|---|---|
| FR | 2 838 047 A1 | 10/2003 |
| WO | 2005/114155 A1 | 12/2005 |
| WO | 2007/070487 A2 | 6/2007 |
| WO | 2008/004212 A2 | 1/2008 |
| WO | 2008/086628 A1 | 7/2008 |

OTHER PUBLICATIONS

International Search Report from UK Application No. GB0815817.2, Dated Dec. 11, 2008 (1 Page).

* cited by examiner

DEVICE FOR MONITORING THE REMOVAL OF ITEMS PLACED IN COMPARTMENTS OF A BLISTER PACKAGE, IN PARTICULAR TO ASSIST A PATIENT IN FOLLOWING A PRESCRIBED PROGRAMME OF MEDICATION

The invention relates to a device for monitoring the removal of articles contained in compartments of a container of the type known as blister package, in particular to assist a patient in following a prescribed programme of drugs.

In the context of the invention the word "drug" should be understood in its most general meaning: pill, tablets, capsules, etc Nowadays, drugs of this type are often packaged in compartments of a blister package, i.e. a plastic material container comprising a number of sealable compartments having an open side intended to accommodate a drug dosage. These compartments are covered with a breakable cover. The blister pack is covered with a single breakable foil or individual breakable flaps, in order to obtain a tight closure of the compartments and a secure individual packaging. Generally, the compartments are arranged as a matrix configuration including a number of lines and/or columns. Typically the rows can be times of the day and the columns can be days of the week or the month.

The patient, when he wishes (or must) take a medication, breaks the cover (or the surface sheet) to remove the drug contained in the particular compartment.

The blister packs are inexpensive and when all the compartments are empty, can be thrown away. It is thus a disposable device.

Some medical treatments require the taking of drugs at regular intervals: for example, each day at a given hour, even several times per day. Also, the need exist to provide devices to assist a patient in following a prescribed regimen for taking medication.

In known art, many devices exist and these devices are based on various technologies. Moreover, these devices offer a more or less important number of functions: detection of taking of drugs, programmed reminding, data transmission to remote sites, etc.

It must be understood that the function "detection of taking a drug" only means that the drug to be taken is removed from a compartment of the blister package, following the break of the compartment cover by the patient. As a matter of facts, it is not possible to ensure that the patient really takes this drug.

In the context of the applications aimed by the invention (drugs conditioned in a blister package) prior art devices allowing monitoring or detection functions are associated with electric, electronic or optical detection means, which are external to the blister package or integrated in the package.

The principal technologies employed in prior art devices are described in the documents below which utilise electric/electronic (generally based on resistance or conductivity change detection [for example on/off mode], etc) or optical detection circuits.

In a first mode of realization, the blister package is modified (i.e. non-standard type) and includes an additional layer (flexible printed circuit) provided with conducting or resistive tracks placed under the compartment. When one of the compartments is opened and the drug removed, this action precipitates a rupture of the electric circuits of the zone underlaying this compartment. Electronic circuits placed on this layer or in an external electronic module detect a change in resistance or conductance, which means that a drug was removed. A particular configuration of the tracks can also make it possible to determine the co-ordinates of the compartment, i.e. what drugs is removed. Such a device is described, for example, in the American patent application US 2006/0144747 A1 (Thanhuhung Le et al.).

The drawback of this type of solution is that it is necessary either to modify the blister package structure (non-standard package), or to provide an additional printed circuit layer. As mentioned above the blister package is a disposable device and is thrown when it is empty. Thus said first solution increases the cost of the blister package, in particular if the electronic detection circuits are integrated into the blister package. If the printed circuits layer is external to the blister package, said layer is also a disposable component. Moreover, in both cases, it is necessary to provide an electrical connector to connect the printed circuits layer to electronic external circuits (display unit, sound warning, signals transmission circuits linked to a remote site, etc). The printed circuit layer and the connector components add expense to what is necessarily a disposable package.

A device including external detection means consisting in a plurality of micro-switches has also been proposed in the prior art. Said micro-switches are located closed to each compartment. Each micro-switch generates an output on/off electrical signal detecting the passage of a drug through a channel when it is removed from the compartment. It is also possible to monitor the co-ordinates of the compartment.

Such a device is described in the German patent DE 41 34237 C1 (Simon, Udo).

The advantage of such a device is the possibility to accommodate standard blisters packages, i.e. without any structure modification (as-marketed blister packages). Furthermore, it does not imply use of any disposable component, except standard blister packages when empty.

However, this solution presents a drawback, because the reliability of electric components (micro-switches) not satisfying (in particular change in conductivity behaviour after some time).

In prior art, devices implementing optical solutions have also been proposed. In such devices, a couple of optoelectronic components (emitter and receiver components) are provided and located in opposite for each compartment, in order to detect the presence or the absence of a drug in the aforementioned compartment. When a drug is removed, it is also possible to determine the co-ordinates of the compartment.

Such a device is described, for example, in the German patent application DE 38 18705 A1 (Jurgens Olaf) or in the French patent application FR 2 838 047 A1 (TAM TELE-SANTE LTD.).

As previously, the advantage of these devices is to accommodate standard blister packages, i.e. without modification of structure. Again; they do not imply use of any disposable component, except standard blister packages when empty. Moreover, an optical solution has a greater reliability than an electric one.

However, this solution presents the following drawbacks:

This solution requires two different optoelectronic components per compartment and, especially, the detection can be disturbed by the daylight, which does not allow, in practice, to obtain a high reliability level which is theoretically associated with an optical technology.

It follows that the parasitic effects of daylight need to be compensated. In the above-mentioned French patent application FR 2 838 047 A1, the emitted light is pulsated in order to remove the parasitic effects of the daylight in the detection stages of the electronic circuits. These provisions increase the complexity and the cost of the electronic circuits.

The need thus exists to provide a device assisting a patient in following a prescribed regimen for taking drugs, said device accepting standard blister packages (i.e. as-marketed blister packages), multi-purpose, of low complexity and low cost, and offering a high degree of reliability.

It is the principal object of the invention.

With this respect, the device according to the invention implements an optical technology, which offers a great reliability, but uses in an advantageous manner, daylight as source of illumination.

The device according to the invention makes it possible to detect the opening of a cover of compartment in which is located a drugs by reception of daylight energy. This one is detected by a photosensitive sensor located under the compartment. The device includes an opaque material support, which acts as a container to accommodate a standard blister package and which occults the transparent faces of each compartment, in order to avoid an erroneous opening detection when a cover is closed. The photosensitive sensors are connected to electronic circuits processing the output signals. The important changes of the output signals (a priori "on/off" mode) indicate the opening of a compartment and that daylight has impinged onto the optical sensor. Each sensor being associated only one cell, it is also possible to know its position in the blister package, and thus what drugs are removed.

The device according to the invention makes it possible to overcome the drawbacks of devices of the prior art, some of which have been referred to above, while preserving the advantages inherent to these devices, in particular those allowed by an optical solution.

Naturally, as in the most advantageous case of the prior art, the device according to the invention does not require any modification of the existing packaging and is reusable. Reliability is increased; the reliability of the optical components being higher than the one of the electrical technology. It is not a complex and costly solution thanks to the very low cost of the optical photodiodes components.

But compared to the devices of the prior art, a device according to the invention has the main following additional advantages:

- It only needs a single optical component per compartment for the detection of taking of drug;
- It offers the high reliability of optical components even in presence of parasitic light radiation thanks to technical features eliminating these radiations: the walls between compartments being opaque;
- It allows the combined delivery of varied drugs because it can be adapted to accommodate blister compartments of various sizes; and
- It can rest or be used in any position, because it is entirely insensitive with the position of the drugs in the cells.

Finally, although the invention preferentially relates to the medical field, other types applications are possible. The device according to the invention can accommodate all standard blister packages comprising at least one compartment, which shapes and sizes are unspecified, containing items similar to drugs (pastilles, candies, etc). It makes it possible to detect the removal of these items out of a compartment.

The main subject of the invention is a device for monitoring the removal of articles conditioned in compartments of a container of the type known as blister package, said blister package comprising a plurality of compartments containing each at least one article, characterized in that at least the bottom walls of said compartments are transparent to daylight and said compartments are provided with an opaque breakable cover in order to render them accessible for article removal, that said device comprises a plate supporting a body comprising open cavities adapted to receive said plurality of compartments of said blister package, that the walls of said cavities located between said compartments are opaque and the bottom walls of said cavities comprise at least a transparent region, that an array of photoelectric sensors sensitive to daylight wavelengths and delivering output electrical signals is implemented on said support, one per compartment, each photoelectric sensor being adjacent to said transparent region such that the removal of an article out of a compartment authorizes daylight penetrating into the cavity receiving said compartment, illuminating the photoelectric sensor associated to said cavity and causing a change of the level of said output electrical signals, and in that said device comprises detecting circuits sensing said level change in order to monitor said removal of article.

Figure 1B:
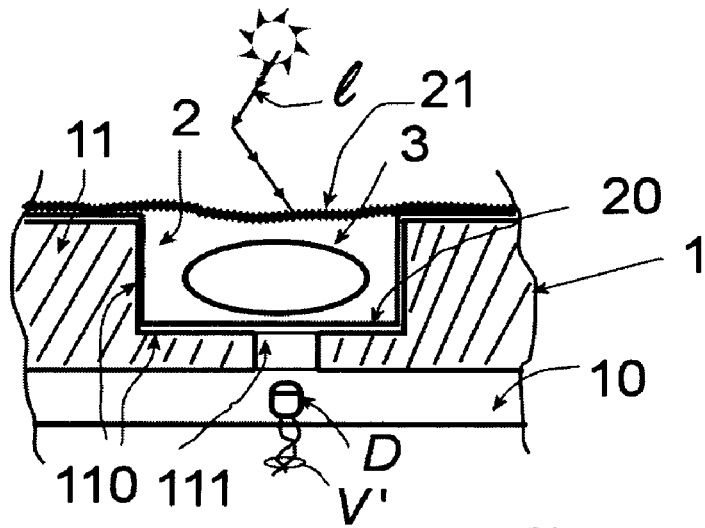
Figure 1C:
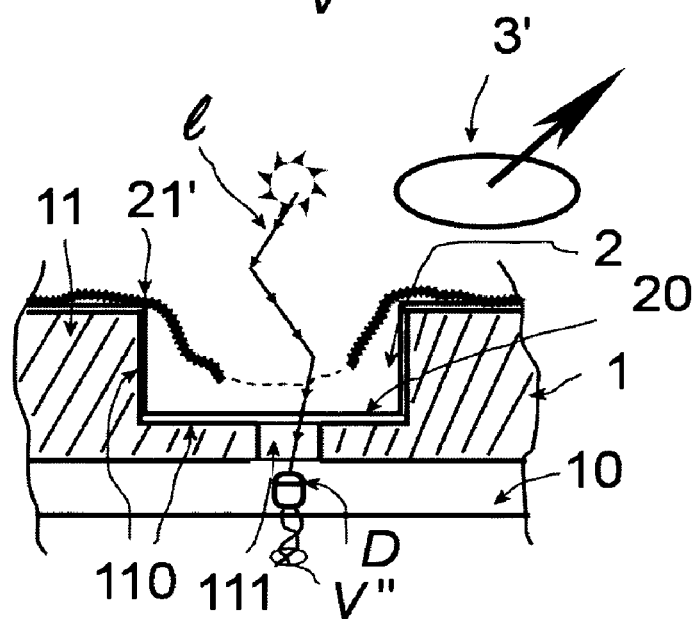
Figure 2:
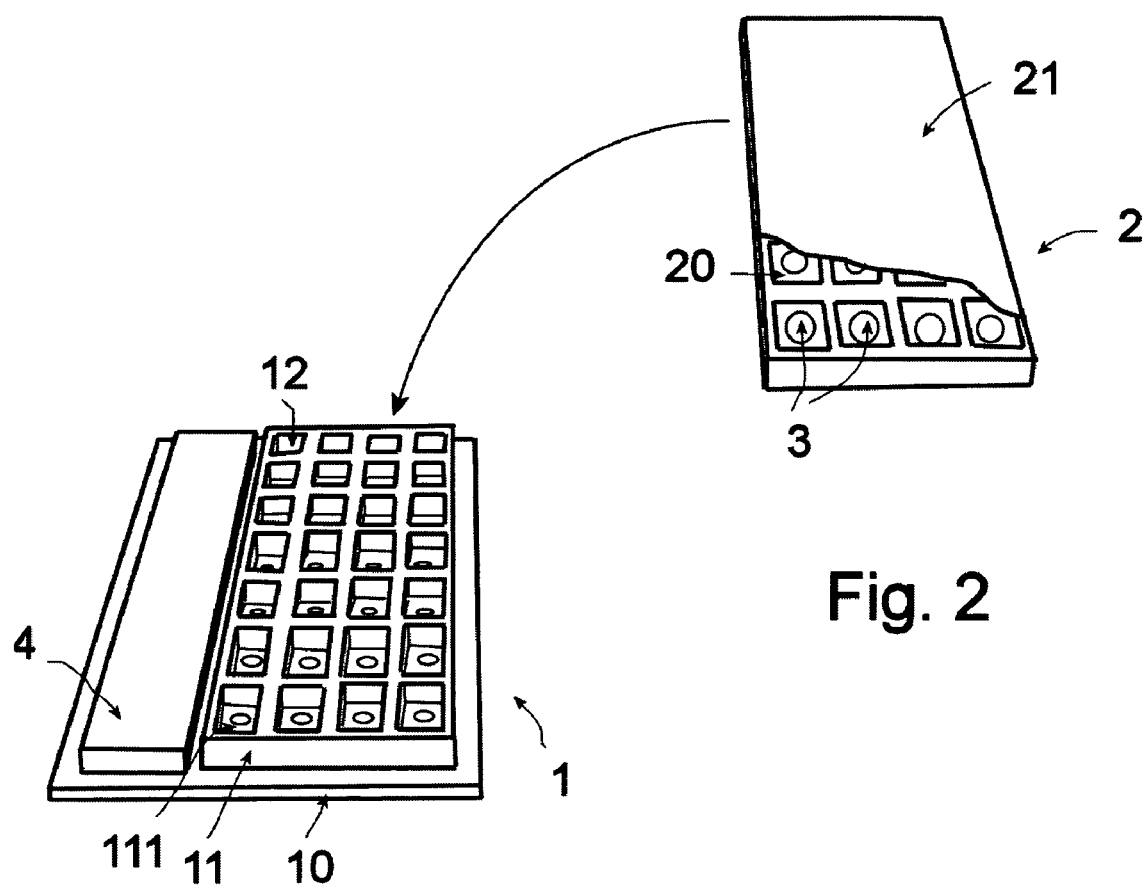
Figure 3:
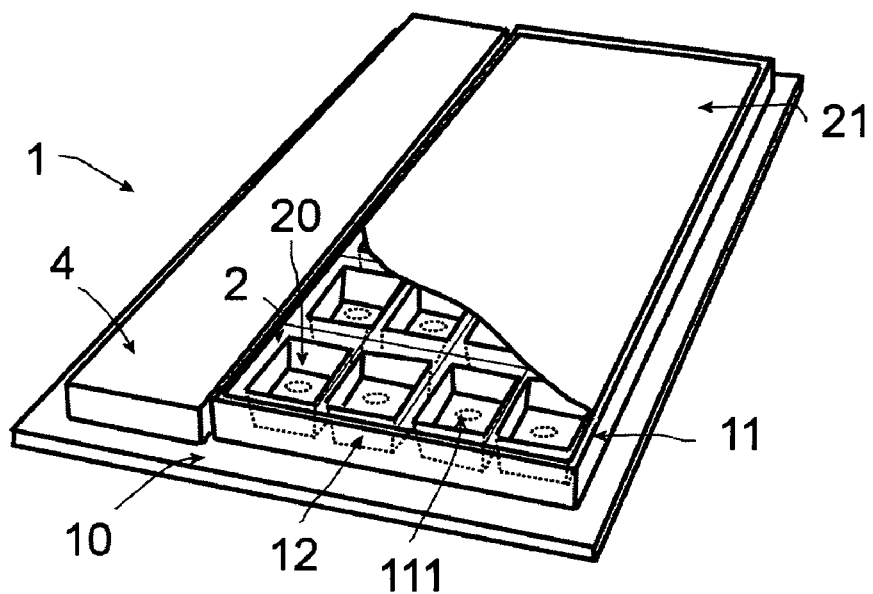
Figure 4:
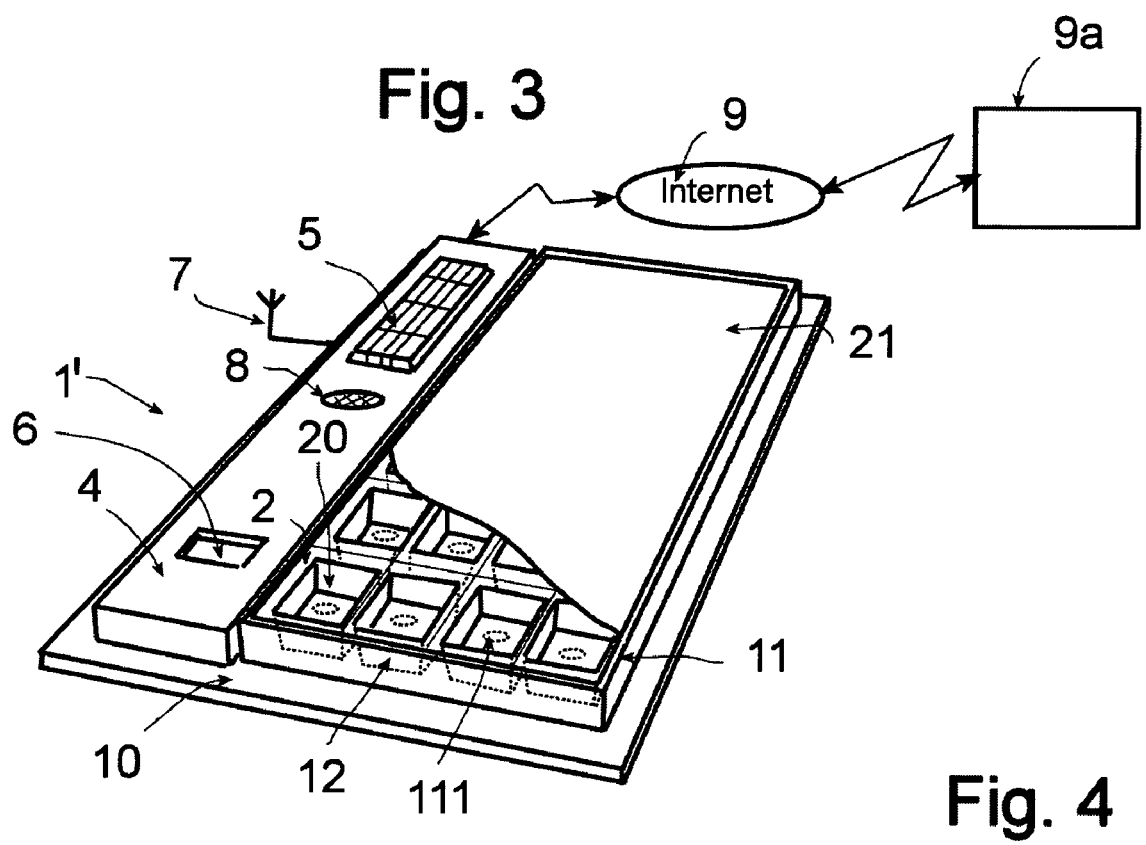

The invention now will be described in a more detailed way while referring to the annexed drawings, among which:

FIGS. 1A-1C schematically illustrate the main technical features and the principle of operation of a device to assist a patient in following a prescribed regimen for taking drugs according to the invention;

FIG. 2 schematically illustrates a complete device for assisting a patient in following a prescribed regimen for taking drugs according to a preferred embodiment of the invention before the insertion of a blister package into the device;

FIG. 3 schematically illustrates the device of FIG. 2 ready to be used containing the blister package inside; and FIG. 4 schematically illustrates a device for assisting a patient in following a prescribed regimen for taking drugs according to an alternate embodiment offering various functionalities.

The following shall focus, without restricting the scope of the present invention in any way, on the context of the preferred application of the invention, unless specified to the contrary, i.e. in the case of drugs conditioned in a standard blister package and with the assistance with the taking of one or more of these drugs contained in a compartment of the aforesaid blister package.

In order to simplify the description, without limiting in anything the scope of the invention, the word "pill" will be employed hereafter to designate the aforementioned drugs.

The main characteristics and the mode of operation of a device according to the invention will be now detailed taking into consideration FIGS. 1A to 1C.

FIG. 1A is a partial cut view of a device 1 for assisting a patient in following a prescribed regimen for taking drugs according to the invention. It includes a lower plate 10, for example a printed circuit layer and an upper body 11 made of material opaque to the light, and in particular to daylight l. Said body 11 includes a plurality of open cavities 12. As illustrated by FIGS. 1B and 1C, each cavity 12 is intended to receive one compartment 20 of a standard blister package 2.

The bottom wall of each compartment 12 comprises a region 111 made of transparent material to daylight l or comprises an open channel communicating with the printed circuit layer 10. Except for this transparent or open region 111, other walls 110 of cavity 12 are opaque.

On the printed circuit 10 are implemented a plurality of photoelectric sensors D, sensitive to daylight wavelengths, for example photodiodes, delivering output electric signals V transmitted to processing electronic circuits (not shown in FIGS. 1A-1C). Said electronic circuit are well known per se for those skilled in the art. Each photodiode D located adjacent to a transparent zone 111 and receives the natural light l as the cavity is empty in the state illustrated in FIG. 1A. It thus delivers in this state an output signal V of a first level (i.e. "illumination level").

The cavities 12 are adapted (dimensions and shape) to receive the compartments 12 of the blister package 2. At least the bottom walls of those are transparent, in whole or part; to daylight 1. Body 11 thus forms a mechanical supporting frame for the blister package 2.

FIG. 1B illustrates the blister 2 inserted into the device 1. Each compartment 20 contains one or more pills 3. Compartments 12 are covered with a cover 21 consisting of a rupturable continuous foil or individual flaps. Said cover 21 is opaque to daylight 1 and, for example, is made out of a thin aluminium foil or any other suitable metal foil. This provision makes it possible to avoid daylight 1 penetrating into cavity 12, walls 110 being also opaque. The photodiode D delivers an output signal V' of a second level (i.e. "darkness level").

When a patient tears a cover, state referred 21', and that pill 3 is removed, state referred 3', daylight 1 can again impinges onto photodiode D. This one delivers a signal V'' of a third level. The bottom wall of cell 20 being transparent, the level of signal V' is equal to the level of signal V, at least not very different. When cover 21 is torn and pill 3 is removed from compartment 12 (state 3'), a strong change of the level of output signal delivered by photodiode D occurs. Said signal change can be detected by electronic circuits (not shown in FIG. 1C). It corresponds to a particular cavity 12 and thus also to a particular compartment 20 of the blister package 2.

The characteristics of the device for assisting a patient in following a prescribed regimen for taking drugs according to the invention which provides an optical insulation of compartments 12 thanks to opaque walls 110 make it possible to be freed from any effect of parasitic light, in a simple manner, without requiring any compensating circuits. Moreover, the advantageous use of daylight 1 as source of illumination makes it possible to use a single sensor per compartment 20 of the blister package 2.

Now, two embodiments of a device for assisting a patient in following a prescribed regimen for taking drugs according to the invention will be described per reference to FIGS. 2 to 4.

The items of FIGS. 2 to 4 common to FIGS. 1A to 1C carry the same references and will be again described only as a need.

FIG. 2 illustrates a first complete embodiment of a device 1 according to a preferred mode of realization of the invention before insertion of a blister package 2 into support 11. This one, as it was described, comprises a plurality of cavities 12 adapted to receive compartments 20 of blister package 2. The lower plate 10 consists, for example, in a printed circuit layer on which are implemented a plurality of photodiodes D (FIGS. 1A to 1C).

The blister package 2 is made out transparent plastic, at least the bottom walls of the compartments 20, which are covered with an opaque ruptable foil 21 to authorize removing of pills.

The photoelectric sensors may consist in an array of detectors, preferably in technology so-called "SMD" ("Surface Mount Device").

An electronic module 4 including processing circuits is also implemented onto said printed circuit layer 10. Said module 4 receives and processes signals delivered by photodiodes D (FIGS. 1A with 1C). It can consist, for example, in a data processing unit including a microprocessor and memory means. Per se, such circuits are well-known for those skilled in the art and do not require a more detailed description. These circuits allow, in addition to the processing of signals delivered by photodiodes D, various complementary functions, for example generation of local and/or remote alarms to remind the patient to take a given drug and/or transmitting information to authorized entities (doctors, nurses, etc) concerned with the prescribed medical regimen.

FIG. 3 illustrates the device of FIG. 2 after insertion of the blister package 2 into the compartment support 11. The foil or covers 21 obturing compartments 12 were partially removed in this figure to let shown some compartments 20 in cavities 12 and associated transparent zones 111.

FIG. 4 illustrates a second embodiment corresponding to an alternate mode of realization of the device for assisting a patient in following a prescribed regimen for taking drugs, referred 1', offering a plurality of complementary functions: entering data (for example relating to a required time to taking a drug, etc.) and/or parameters to program device 1', for example using keyboard 5, displaying entered data and/or generation of visual alarms, for example using a LCD display unit 6, generation of acoustical alarms in relation with the removal of a pill or as a reminder, for example using a loudspeaker 8.

Device 1' can also include radio electric communication means, symbolized in FIG. 4 by an antenna 7, in order to transmit data to a remote site (not shown: hospital, etc). Device 1' can also be connected to a remote site 9a via a data transmission network, for example via Internet 9 or via any other type of remote network (WLAN) or local network (WIFI, Ethernet, etc).

The above mentioned data links can also be used to configure or to program device 1'. This configuration can also be obtained by reading information on a label of the type "barcode" or "RFID" attached to the blister package 2. It is only necessary to provide a suitable reader unit (not shown in FIG. 4) integrated in the electronic module 4 or an autonomous reader connected to said module 4. The configuration, whatever the mode used, can include in particular information such as the name and address of the patient, the name of the doctor, the nature of the drugs to be taken, quantity and hours of drugs taking, etc, that for each compartment 20. These configuration data are memorized in memory means (not shown in FIG. 4) located in the electronic module 4.

Per se, the electronic circuits necessary for the implementation of the afore-said functions are well-known of skilled in the art and do not require to be more amply described.

By reading the above, it is easy to establish that the invention effectively achieves its set objectives, and which it is useless to recall.

However, It should however be made clear that the invention is not restricted to the sole examples of embodiments explicitly described, notably in relation with FIGS. 1A to 4. The device for assisting a patient in following a prescribed regimen for taking drugs is in particular suitable for be associated other functionalities known per se that those described in these figures.

Finally, as it was already specified, although the application to the field of medicine constitutes the preferred application, the device according to the invention can be implemented for monitoring the removal of any article out of a compartment of a standard blister package, provided that said blister package is initially covered with a continuous film or covers opaque to daylight and occulting the aforementioned compartment, in order to avoid that daylight impinges onto the photo sensors when the blister package is inserted into the device.

The invention claimed is:

1. A device for monitoring the removal of articles contained in compartments of a container of the type known as blister package, said blister package comprising:

a plurality of compartments containing each at least one article, wherein at least the bottom walls of said compartments are transparent to daylight and said compartments are provided with an opaque rupturable cover in order to render them accessible for article removal, said device comprises a plate supporting a body comprising open cavities adapted to receive said plurality of compartments of said blister package, the walls of said cavities located between said compartments are opaque and the bottom walls of said cavities comprise at least a transparent region, an array of photoelectric sensors sensitive to daylight wavelengths and delivering output electrical signals is implemented on said support, one per compartment, each photoelectric sensor being adjacent to said transparent region such that the removal of an article out of a compartment authorizes daylight penetrating into said the cavity receiving said compartment, illuminating the photoelectric sensor associated with said cavity and causing a change of the level of said output electrical signals; and wherein said device comprises detecting circuits sensing said level change in order to monitor said removal of article.

2. A device according to claim 1, wherein said blister package is of a standard as-marketed type comprising a plastic housing including said plurality of compartments and a cover comprising an opaque foil.

3. A device according to claim 2, wherein said opaque foil is a thin metallic foil.

4. A device according to claim 1, wherein said photoelectric sensors comprise an array photodiodes.

5. A device according to claim 4, wherein said array of photodiodes are built in the so-called technology "surface mounting device".

6. A device according to claim 1, wherein said detecting circuits sensing said change in said output electrical signals delivered by said photoelectric sensors are located in an electronic module implemented on said plate supporting said body.

7. A device according to claim 6, wherein said electronic module comprises a data processing unit comprising a microprocessor and memory means.

8. A device according to claim 7, wherein said electronic module further comprises:
  a keyboard to enter data and/or programming parameters,
  a LCD display unit to display said data and/or parameters,
  a loudspeaker to generate acoustic alarms; and
  means connecting said device to a remote site via a data transmission network in order to send and/or receive data and/or programming parameters.

9. A device according to claim 6, wherein said blister package comprises means storing data identifying its content and/or parameters associated to said articles and that said electronic module includes or is connected to a reader unit adapted to acquire said identifying data.

10. A device according to claim 1, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

11. A device according to claim 2, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

12. A device according to claim 3, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

13. A device according to claim 4, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

14. A device according to claim 5, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

15. A device according to claim 6, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

16. A device according to claim 7, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

17. A device according to claim 8, wherein, said articles comprise drugs, said blister package comprising a plurality of compartments and each compartment being designed to hold at least one drug, said electronic detecting circuits comprise means to sense the removal of said drugs, in order to assist a patient in following a prescribed regimen for taking drugs.

* * * * *